United States Patent [19]
Schmidt et al.

[11] Patent Number: 5,395,674
[45] Date of Patent: Mar. 7, 1995

[54] SHOCK ABSORBING SHEET MATERIAL

[76] Inventors: K. Michael Schmidt, 295 Grandview Dr., Woodside, Calif. 94062; Claude A. S. Hamrick, 19570 Montevina Rd., Los Gatos, Calif. 95030

[21] Appl. No.: 993,099

[22] Filed: Dec. 18, 1992

[51] Int. Cl.[6] .......................... B32B 1/00; A61F 5/44
[52] U.S. Cl. ..................................... 428/178; 428/76; 428/172; 428/212; 428/192; 5/455; 128/918; 604/346
[58] Field of Search ............... 428/178, 76, 137, 172, 428/188, 212, 141, 192; 5/449, 471, 455, 448, 461, 468; 128/918; 604/346; 36/29, 30 R, 44, 37

[56] References Cited

U.S. PATENT DOCUMENTS

| | | | |
|---|---|---|---|
| 4,096,306 | 6/1978 | Larson | 428/178 |
| 4,203,268 | 5/1980 | Gladden et al. | 428/178 |
| 4,287,250 | 9/1981 | Rudy | 428/178 |
| 4,422,194 | 12/1983 | Viesturs et al. | 5/441 |
| 4,869,939 | 9/1989 | Santo | 428/178 |
| 5,030,495 | 7/1991 | Neu | 428/172 |
| 5,110,660 | 5/1992 | Wolf et al. | 428/178 |

Primary Examiner—Donald J. Loney
Attorney, Agent, or Firm—Claude A. S. Hamrick

[57] ABSTRACT

Shock absorbing sheet material including a sheet of resilient material having a plurality of surface deformations configured to form bubble-like chambers of a first relatively large volume communicatively interconnected through small passageways to similar surface deformations forming relatively smaller chambers. The larger chambers are intended to extend substantially farther out of the sheet mid-plane than are the smaller chambers, such that, in response to the application of a compressive force to the sheet, the applying member will first engage the larger bubbles causing them to resiliently deform and, in so doing, cause a displaced volume of fluid contained therein to flow through the passageways and enter the smaller chambers causing them to distend outwardly to be engaged by the compression force-applying member, at which time both large and small chambers resiliently resist the compressive forces.

15 Claims, 6 Drawing Sheets

PLAN VIEW Fig. 2d

SHOCK ABSORBING SHEET MATERIAL

BACKGROUND OF THE INVENTION

1. Field of the Invention

The present invention relates generally to shock absorbing padding materials and the like, and more particularly to an improved shock absorbing sheet material having a plurality of small, active pumping elements formed therein including chambers of different sizes interconnected by communicating passageways such that a compressive force applying member engaging the material will first contact a wall forming one of the larger chambers causing it to collapse resiliently and pressurize a connected smaller chamber which expands and is subsequently engaged by the compressing member, and the two thereafter jointly exert resilient resistance to continued compression of the sheet material.

2. Brief Description of the Prior Art

Prior art sheet materials and pads include various types of gas-containing chambers intended to resiliently resist compression of the material and thereby perform shock-absorbing or dampening functions. Examples include bubble-pack packing materials, honeycomb pads, and simple sponge-configured pads such as the type used under carpet. However, in all such materials a compressive force applied thereto will experience a more or less uniform resistance as the resilient material and/or entrained gases are compressed. This causes the material to react in a manner similar to an undamped spring. In many applications, shock absorbing performance could be improved if the reactance of the pad had a non-linear characteristic, that is, if in response to the application of a uniform compressive force the pad resisted in a stepped or non-linear fashion. For example, in the case of shoe sole applications the anatomical impact experienced by the wearer of the shoes could be improved by causing the foot to experience a non-linear deceleration before it bottoms out as the sole reaches maximum compression.

SUMMARY OF THE PRESENT INVENTION

It is therefore a principal objective of the present invention to provide an improved sheet material, the resistance to compression of which is nonlinear and in fact may have a stepped response characteristic.

Another objective of the present invention is to provide a new configuration for shock-absorbing, damping or redistributing materials which can be used in a multitude of applications.

Briefly, a presently preferred embodiment of the present invention includes a sheet of resilient material having a plurality of internal voids or surface deformations configured to form bubble-like chambers of a first relatively large volume communicatively interconnected through small passageways to related voids or surface deformations forming relatively smaller chambers. The larger chambers are intended to extend substantially farther out of the sheet mid-plane than are the smaller chambers, such that, in response to the application of a compressive force to the sheet, the applying member will first engage the larger bubbles causing them to resiliently deform and, in so doing, cause a displaced volume of fluid contained therein to flow through the passageways and enter the smaller chambers causing them to distend outwardly to be engaged by the compression force-applying member, at which time both large and small chambers resiliently resist the compressive forces.

A principal advantage of the present invention is that its compression characteristics provide a progressive rate of deceleration to the force applying member and thus reduce the shock experienced by the member as it moves from initial engagement to full stop.

Another advantage of the present invention is that it provides a means for transferring large area compressive forces to smaller areas to achieve unusual results.

These and other objects and advantages of the present invention will no doubt become apparent to those skilled in the art after having read the following detailed description of the preferred embodiments illustrated in the several figures of the drawing.

DETAILED DESCRIPTION OF THE PREFERRED EMBODIMENTS

Figure 1:
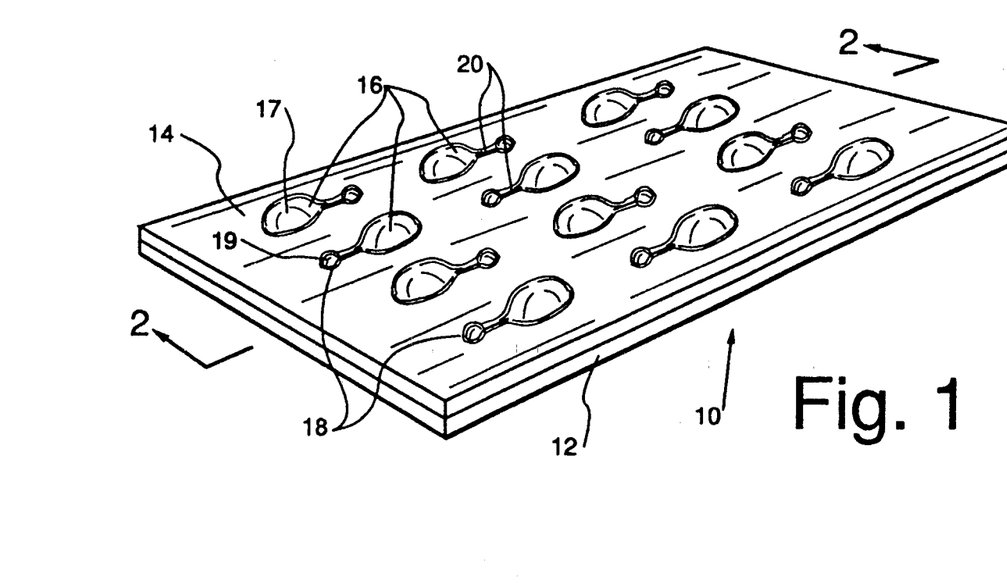
FIG. 1 is a perspective view illustrating one embodiment of the present invention.

Referring now to FIG. 1 of the drawing, a sheet of shock absorbing material in accordance with the present invention is illustrated at 10, and as depicted includes a flat or planar configured base sheet 12 overlaid by a top sheet 14 of resilient or elastic material deformed upwardly at regular intervals to define upwardly extending but downwardly open relatively large bubbles 16 forming cavities 17, and adjacent smaller bubbles 18 forming cavities 19, the two being joined together by communicating channels 20. The upper sheet 14 is glued or otherwise bonded to the lower base sheet 12 so as to close the cavities and form the relatively large chambers 17 beneath the deformed surface portions 16 and the relatively small chambers 19 beneath the smaller deformations 18. The chambers 17 and 19 of each large/small pair are inter-communicated by a passageway formed by the channel 20 as it is closed on the lower side by the base 12. Note that the cavity pairs are organized and oriented to achieve maximum density over the upper surface area of the pad.

Although the chamber sizes are depicted in FIG. 1 as large compared to the size of the sheet, it is to be understood that, depending on the intended application, the "large" chambers can range from small fractions of an inch in diameter to several inches in diameter. The dimensions of the smaller chambers would be scaled proportionally smaller. Similarly, the thickness of the sheet or sheets 12, 14 can range from extremely thin membrane thicknesses to large thicknesses of several inches or more.

Figure 2A:
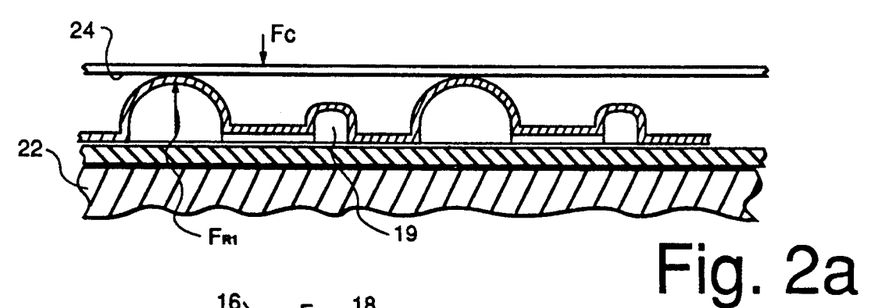
FIGS. 2a, 2b, and 2c are cross-sections taken along the line 2—2 of FIG. 1 to illustrate in successive fashion the nonlinear compression resistance characteristic of the present invention.
Figure 2B:
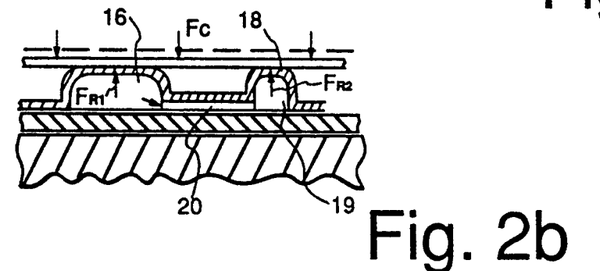
Figure 2C:
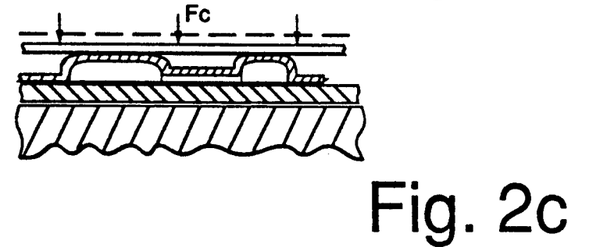

Referring now to FIG. 2a, which is a partial cross-section taken along the line 2—2 of FIG. 1, it will be observed that if the pad is laid upon a planar supporting surface 22 and a compressive force $F_C$ is applied to the top of the pad by means of a planar member 24, the larger chamber forming bubbles 16 will be engaged and will initially resiliently resist the compression. However, as they are compressed, as depicted in FIG. 2b, the air or other fluid contained within the bubbles 16 will be forced through channels 20 into the smaller chambers 19 causing the bubbles 18 to expand and rise up to be engaged by the surface 24. This is to say that as bubbles 16 are collapsed they exert an upwardly directed resisting force $F_{R1}$ upon the surface 24. At this point, further downward movement of the member 24 will cause both bubbles 16 and 18 to be resiliently collapsed, as depicted in FIG. 2c, with a second resisting force $F_{R2}$ being additionally exerted by the bubble 18 of each pair. It will thus be noted that the resilient resistance to compression is nonlinear and in fact tends to operate in step-like fashion as the sheet is compressed. That is, during the initial stage of compression the resisting force $F_{R1}$ is generated as the fluid within chamber 17 is compressed and as the smaller bubble 18 is expanded upwardly; during the second stage of compression, the two bubbles 16 and 18 are simultaneously compressed and jointly exert a total resisting force $F_{RT}=F_{R1}+F_{R2}$, as the pad is driven to maximum compression as illustrated in FIG. 2c.

Figure 2D:
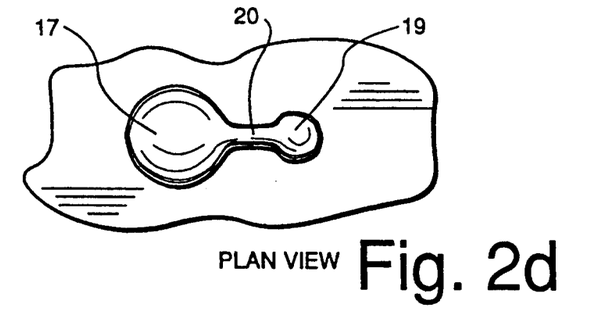
FIG. 2d is a plan view of the embodiment depicted in FIGS. 2a–2c.

A plan view of a typical large cell 17 and small cell 19 pumping unit is illustrated in FIG. 2d.

Figure 3:
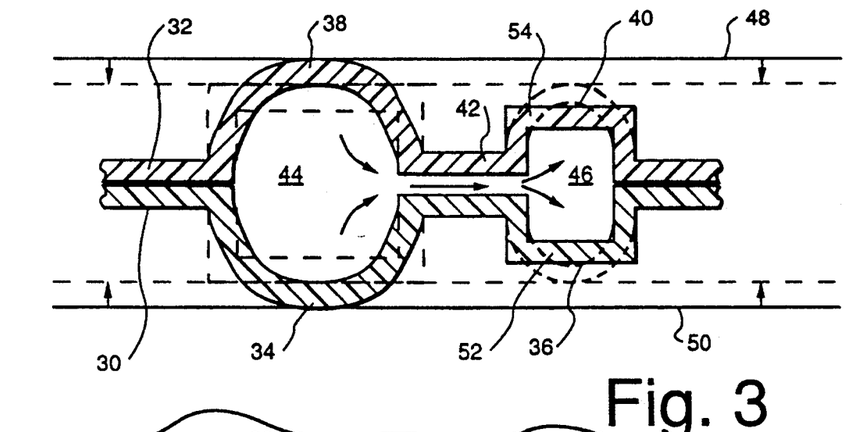
FIG. 3 shows an alternative cross-sectional configuration for an embodiment of the present invention.

Turning now to FIG. 3 of the drawing, a cross-section taken through an alternative embodiment is depicted wherein the bottom layer of material 30, instead of being planar, is deformed to include downwardly extending bubbles 34 and 36 in mirror-image correspondence to the bubbles 38 and 40 of upper sheet 32 such that a greater volume of fluid may be contained within the respective chambers 44 and 46. Note also that at least one of the sheets is provided with channels 42 for communicatively coupling the chambers 44 and 46.

In this configuration, as the larger bubbles are collapsed by engagement between two members 48 and 50, the smaller bubbles expand both upwardly and downwardly to engage the compressing surfaces and provide increased resilient resistance to compression. Note that, whereas the larger bubble shaped deformations 34 and 38 in the upper and lower sheets are generally hemispherical in configuration, the smaller deformations 36 and 40 are configured more pill-box in shape so as to provide surfaces 52 and 54 which will readily expand upwardly and downwardly when subjected to increased internal pressure as would result from compression of the larger bubbles 44.

It should be noted that the smaller chamber 46 need not extend outwardly on both sides of the planes of the sheets 30 and 32. In some applications it may be desirable that the small chambers distend in only one direction.

Figure 4:
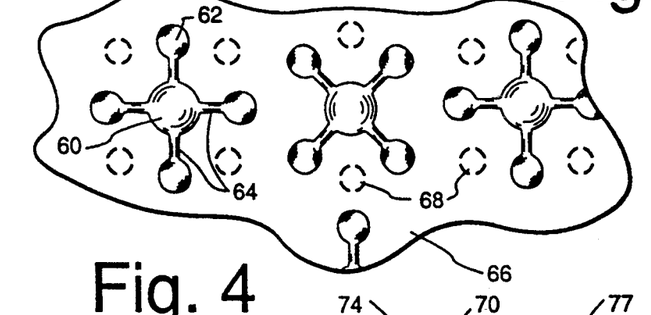
FIG. 4 depicts still another alternative embodiment of the present invention.

In FIG. 4, a plan view of an alternative embodiment of the present invention is depicted in which a plurality of larger central bubbles 60 are each surrounded by an array of smaller satellite bubbles 62 joined thereto by passageways 64. Observe that the large bubble/small bubble combinations, typically formed along the lines described above, are alternately rotated so as to provide a uniform distribution and high density of chambers across the surface of the material 66 forming the pad. In addition, for some applications it may be appropriate to add holes through the sheet material, as shown by the dotted circles 68, to allow air or liquid to pass through the pad from one side to the other.

Figure 5:
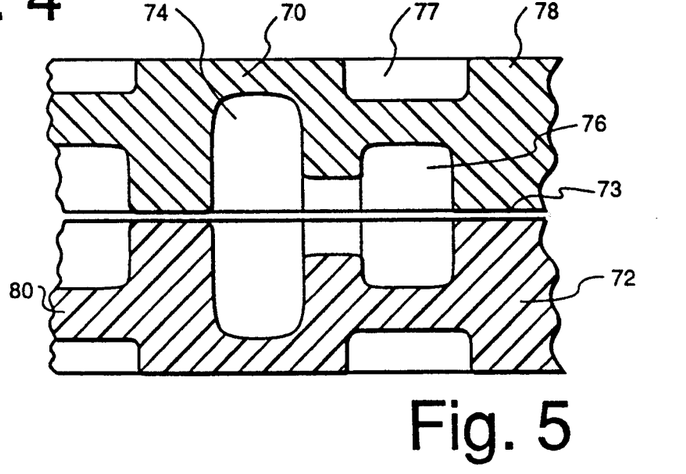
FIGS. 5 and 6 illustrate yet other alternative cross-sectional variations of the present invention.

In FIG. 5, still another configuration of the present invention is depicted in cross-section wherein two sheets of molded compressible material 70 and 72 are joined at 73 to form a substantially flat outer-surfaced pad in accordance with the present invention. Note that in this configuration the large and small chambers 74 and 76, and the communicating channels 78 are molded into the adjacent surfaces of the pads 78 and 80, and small open cavities or depressions 77 and 79 are formed in the outer surface above the smaller chambers in order to allow such chambers to herniate outwardly to meet and engage the compressing surfaces.

Figure 6:
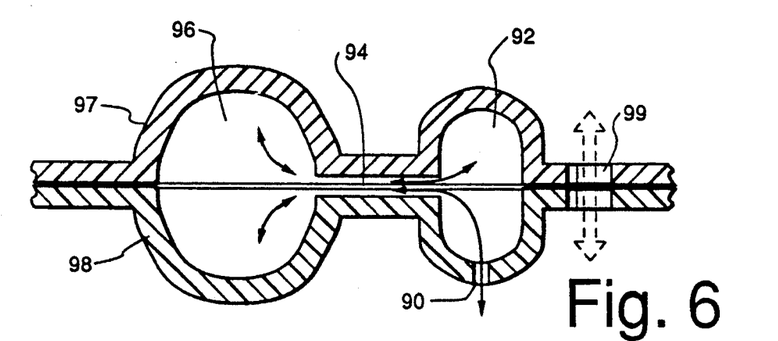

FIG. 6 depicts a further variation of the present invention in a cross-section similar to that of FIG. 3 and includes the addition of an opening 90 in one of the walls forming the small cell 92 which, via passageway 94, is in communication with a larger cell 96. In operation, compression of cell 96 would force air out of passageway 90 and, assuming the materials forming the layers 97 and 98 are sufficiently resilient, removal of the compressive force would allow the materials to return to their undeformed state and cause the expelled air to return through the opening 90. By judicious selection of the size of the hole or holes 90, a throttling function can be effected to modify the damping rate of the shock-absorbing action. As was suggested in the embodiment of FIG. 4, the present embodiment may also include holes 99 to allow air or liquid to pass through the pad formed by the sheets 97 and 98.

Figure 7:
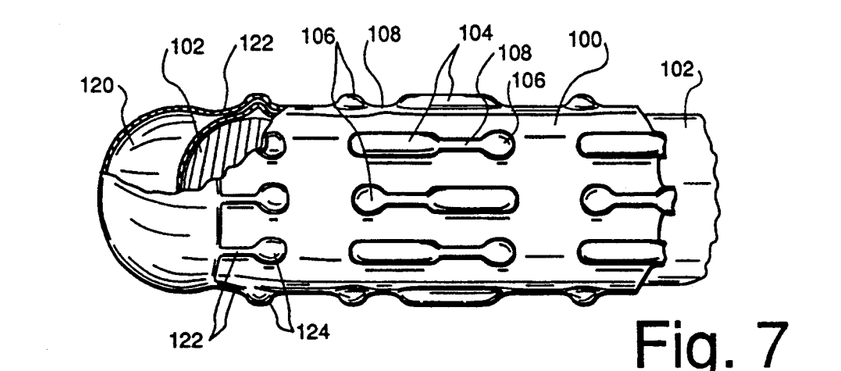
FIG. 7 illustrates an alternative embodiment of the present invention embodied in a condom.
Figure 8:
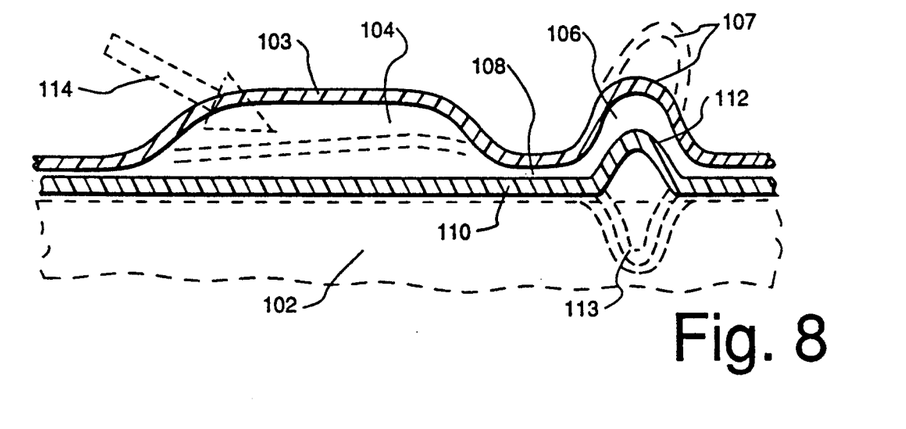
FIG. 8 is a cross-section taken longitudinally through one of the cells of the embodiment of FIG. 7.

Turning now to FIGS. 7 and 8, a particular application of the present invention is depicted wherein multiple cell pairs are suitably arranged in the thin walls of a condom for the purpose of enhancing the sexual experience and aiding penile functionality. As illustrated, the condom 100, which is shown positioned about the distal end of a penis 102, includes a plurality of elongated "large" chambers 104 in communication with "small" chambers 106 by means of small passageways 108, such chambers and passageways being formed by the bonding of thin layers of prophylactic material configured in similar fashion to the previously described embodiments.

In FIG. 8 a longitudinal cross-section taken through one of the cell pairs is illustrated. It will be noted that this embodiment differs from the previous embodiments principally in that the large chamber 104 is elongated, and the underlying membrane 110 is deformed upwardly, as indicated at 112, to nest within the small chamber 106. In use, external forces applied to the resilient wall 103 forming chamber 104, as by engagement with the vaginal wall of the user's partner, as suggested by the arrow 114, would cause chamber 104 to collapse, forcing air or other suitable entrained fluid through passageway 108 into chamber 106. The increase in fluid pressure in chamber 106 would tend to expand the outer wall, as depicted by the dashed lines 107, and would simultaneously cause the inner wall 112 to expand inwardly, as depicted by the dashed lines 113. The resulting localized pressure of the multitude of small chambers upon the penis of the user will result in an unusual sensory experience. Similarly, the outward expansion of the cell wall 107 may likewise result in an additional sensory input to the partner, particularly if the cell 106 is positioned at the upper shank location on the penis so that it engages the partner's clitoral sensory region as the organ is thrust into the vagina.

As indicated in FIG. 7, the several elongated cell pairs are indicated as being alternatingly staggered in position. Alternatively, the cell pairs may be commonly directed and arranged in bands so as to impress a circular constriction force at one or more locations along the length of the penis and perhaps assist in the maintenance of erection. Also depicted in FIG. 7 at the distal end of the condom is an alternative structure in some ways similar to that depicted in FIG. 4 in that it includes a large chamber 120 in communication via passageways 122 with a plurality of smaller chambers 124 surrounding its perimeter. The smaller chambers 124 would preferably be configured similar to the smaller cells depicted in FIG. 8, and could be configured to form a single band circumscribing the end portion of the condom.

In operation, compression and consequent pressurization of the chamber 120 as the user's penis is inserted into the vagina of his partner will cause expansion of the smaller chambers 124 and result in an unusual sensory input to the penile tissues. Similarly, withdrawal will allow chamber 120 to expand and reduce the expansion of the small chambers 124. Although only two types of pumping units are illustrated in FIG. 7, it will be appreciated that numerous other cell configurations and arrays can be designed to enhance the use and functionality of the device.

Figure 9:
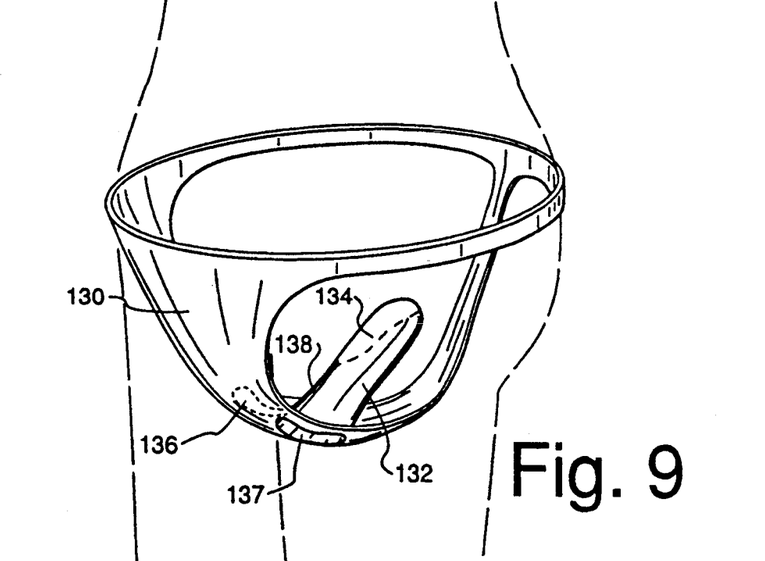
FIGS. 9 and 10 illustrate the provision of a female condom utilizing the present invention.
Figure 10:
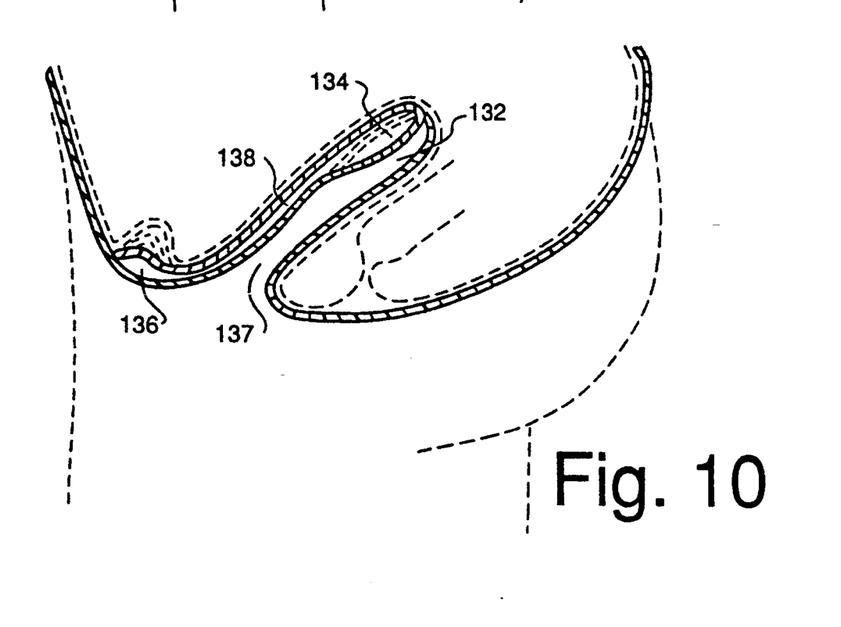

In FIGS. 9 and 10 another application of the present invention is illustrated in the form of a female condom having the novel dual chamber pumping unit adapted to enhance clitoral excitation during intercourse. As depicted in FIG. 9, the female condom is comprised of a bikini style panty 130 housing an inwardly extending tubular projection 132 formed therein in the vaginal contact region. The entire device may be integrally formed of a thin stretchable rubber or plastic membrane, or alternatively, those parts out of the pubic region may be made of another type of woven or synthetic materials. The illustrated embodiment differs from other female condoms, in that in accordance with the present invention a "large" compressible inwardly extending chamber 134 is formed near the distal extremity of the tubular portion 132, a "small" inwardly extending chamber 136 is formed on the inside wall of the panty front just above the opening 134, and a communicating passageway 138 is formed in the upper surface of tubular portion 132 to connect the chamber 134 to the chamber 136.

It will be understood that during intercourse as the partner's penis is thrust into the tube 132 (which extends into the wearer's vagina), the relative large chamber 134, which extends into the distal end portion of tube 132, will be collapsed and force the fluid (a suitable gas or liquid) along passageway 138 and into the smaller chamber 136. Note that chamber 134 protrudes from the exterior side of the panty forming membrane (into tube space 132) while the smaller chamber 136 protrudes from the interior side of the panty material. As a consequence, as chamber 136 extends inwardly during inward penal thrust and relaxes during penal withdrawal, it will periodically apply pressure to the clitoral erogenous zone tending to enhance the likelihood of female climax during intercourse.

Although the illustrated embodiment is depicted to include a single "large" chamber 134 at the upper portion of tube 132, it will be appreciated that a plurality of such chambers could be provided surrounding the tubular member 132. In such case an appropriate network of passageways would be provided to communicate with the smaller chamber (or chamber 136).

Note that although the utility of the several illustrated embodiment of the present invention differ from one to the other, they all share in common the pumping characteristic wherein compression of a larger chamber, or chambers, causes pressurization and enlargement of one or more smaller associated chambers.

Figure 11:
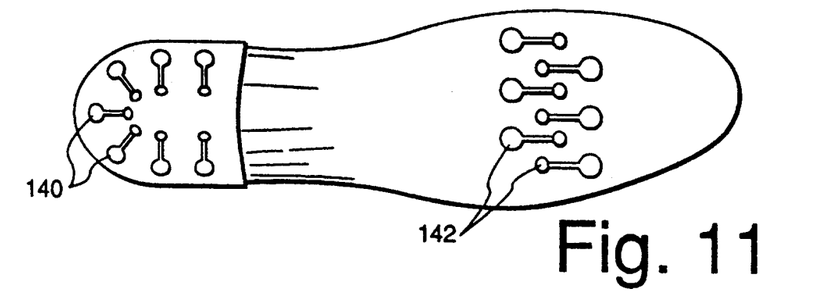
FIGS. 11, 12 and 13 illustrate application of the present invention to shoe soles.
Figure 12:
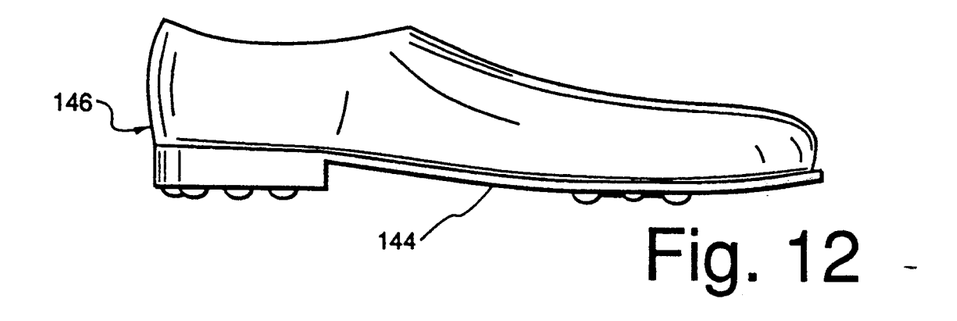

In FIGS. 11 and 12 a further alternative embodiment of the present invention is shown particularly suited for footwear applications. As illustrated, a plurality of the "pumping units" 140 and 142 of the type shown in FIGS. 1-6 are strategically positioned in the heel and metatarsal positions of the outer sole 144 of a shoe 146 to provide superior shock absorption. The large and small "bubbles" act as studs adding to shoe traction while at the same time cushioning the forces applied to the shoe wearer's heel and the balls of his or her feet.

Figure 13:
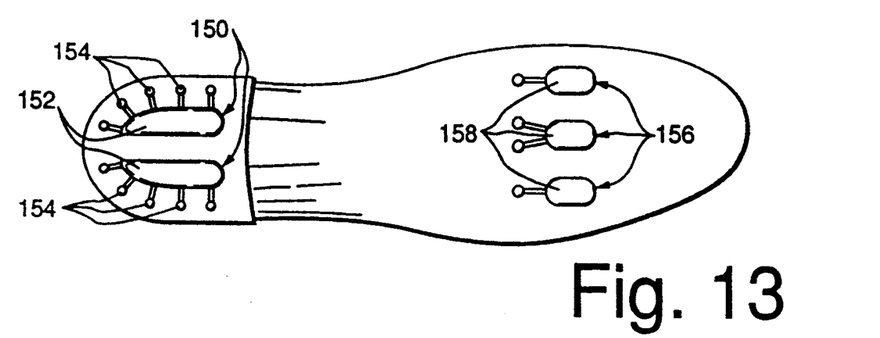

In FIG. 13, yet a further alternative embodiment is depicted which is particularly suited for certain running shoe applications. In this case, a plurality of pumping units are provided in the heel and metatarsal positions. In the heel two multiple small chamber units are provided, as indicated at 150. The larger chambers 152 on each side of the longitudinal centerline of the shoe and the smaller chambers 154 are arranged around the outer perimeter of the heel. These units will, in addition to their shock-absorbing function, serve to provide lateral stability to the heel. The metatarsal units 156 have their large chambers 158 positioned directly under the ball of the foot. The smaller chambers 160 are positioned rearwardly of the chambers 158 so as to provide a forward lift as they are inflated. Those skilled in the shoe art will readily appreciate that various combinations and arrays of the pumping units of the present invention can be used in footwear to add stability and to correct supination and pronation problems.

Furthermore, inexpensive shock-absorbing outer soles can be cut from sheet stock of the type depicted in FIG. 1. Similarly, mid-soles and inner soles can likewise be severed from sheet stock. Material in accordance with the present invention will make superior insoles because of the unique shock-absorbing function, the ease of air circulation (using perforated stock as depicted in FIG. 6) and relief of constant pressure points. As the foot depresses the material, the pumping action of the "units" serves to move air around the foot and relieve pressure points applied to the feet by the shoes.

Still another application of the present invention is in pads for the bed-ridden or handicapped in wheelchairs. By incorporating the pumping units into such pads, living spring-like elements are provided which with every movement redistribute the supporting forces to the body, adding comfort and relief from pressure points. As a result, users will have better circulation and be less prone to experience bed sores of the type common in use of static conventional mattress pads.

As will be appreciated by those skilled in the art, the multi-chambered configurations depicted in the drawing and described hereinabove form small pumping mechanisms which actively resist the collapse or compression of the sheet or other shaped material in which they are formed. The basic principal of the miniature pumps is that air or other fluid trapped in the larger ball-shaped cavities, which in most embodiments protrude from the plane of the sheet, when compressed, will pass the compressed fluid through a narrow channel to a smaller chamber which then expands to meet a compressing surface and add its resisting force to counter the compressing action. By way of example, should a weight be dropped upon a pad of the type depicted in FIGS. 1 and 2, there will be a decelerating effect at a first rate as the weight compresses the larger chambers, forcing fluid into the smaller chambers which expand, rising to meet the weight. As the weight meets the expanded smaller chambers, and tends to compress them along with the larger chambers, the weight will be caused to decelerate at a second rate, etc. Accordingly the functionality of the present invention differs materially from prior art resilient pads, bubble packs and the like.

Although presently preferred embodiments of the present invention have been disclosed above, it is apparent that numerous alterations and modifications of the present invention will become apparent to those skilled in the art after having read this disclosure. It is therefore intended that the appended claims be interpreted as covering all such alterations and modifications as fall within the true spirit and scope of the invention.

What is claimed is:

1. A resilient, generally planar sheet material comprising:
   first deformed portions forming a plurality of first chambers of a first size within said sheet material, said first deformed portions protruding a first distance out of the principal plane of said planar sheet material and containing a fluid;
   second deformed portions forming a plurality of second chambers within said sheet material each of which is of a size substantially smaller than said first chambers, said second deformed portions protruding a second distance less than said first distance out of the principal plane of said planar sheet material, each said second chamber likewise containing the fluid; and
   third deformed portions communicatively linking each said second chamber with one of said first chambers to form a plurality of discrete hermetically sealed units whereby the application of force to said sheet material causes deformation of said first portions, and the deformation thereof causes the fluid contained therein to move from said first chamber into the associated second chambers with the result that the volume of space enclosed by said second portions increases as the force is absorbed.

2. A resilient sheet material as recited in claim 1 wherein said sheet material includes a first layer of resilient material, permanently deformed to form said first chambers, said second chambers, and said communicative passageways, and a second layer of resilient material affixed to said first layer to form closures for each sealed unit formed by particular ones of said first chambers, said second chambers, and said communicative passageways.

3. A resilient sheet material as recited in claim 2 wherein said second layer is deformed in portions corresponding to at least one of said first, second and third portions of said first layer such that the deformations in each layer combine to form said first chambers, said second chambers, and said communicating passageways.

4. A resilient sheet material as recited in claim 1 wherein deforming forces applied on one side of said sheet material to said first chambers causes said second chambers to deform outwardly on the opposite side of said sheet material.

5. A resilient sheet material as recited in claim 2 wherein each said first chamber is communicatively coupled to two or more of said second chambers.

6. A resilient sheet material as recited in claim 5 wherein each said first chamber has a plurality of said second chambers disposed in an array around the perimeter of said first chamber and communicatively coupled thereto.

7. A resilient sheet material as recited in claim 1 wherein perforations are formed in said sheet material between adjacent chambers to allow air to pass from one side of the sheet material to the other.

8. A resilient sheet material as recited in claim 1 wherein the outer perimeter of said sheet material is configured to form at least part of a shock-absorbing pad for footwear.

9. A resilient sheet material as recited in claim 8 wherein said material has a generally D-shaped outer perimeter to form a heel pad for a shoe and includes at least one first chamber located proximate the center of the D-shaped heel pad and a plurality of second chambers communicatively connected to said first chamber and disposed proximate a perimeter edge of said D-shaped heel pad.

10. A resilient sheet material as recited in claim 8 wherein said outer perimeter is shaped to conform to the sole of a shoe and wherein said first chambers are disposed in that part of the sole-shaped sheet material which would correspond to the sole portion that would lie under the metatarsal support region of the pad and said second chambers are positioned on the side of said first chambers closest to the portion of said sole-shaped sheet material which would correspond to the sole portion that would lie beneath the heel support region of the pad.

11. A resilient sheet material as recited in claim 1 wherein said sheet material is shaped at least in part to form the tubular part of a condom device.

12. A resilient sheet material as recited in claim 11 wherein said tubular part of said condom device is configured to enclose a male sexual organ.

13. A resilient sheet material as recited in claim 11 wherein said condom device is configured to be worn by a female user and said tubular part includes a cylindrical projection open at one end and closed at an opposite end, the closed end being intended to extend into the vaginal cavity of the user.

14. A resilient sheet material as recited in claim 13 wherein said projection includes at least one of said first chambers disposed proximate said closed end and communicatively coupled to at least one of said second chambers disposed proximate said open end and intended to be positioned in the clitoral region of the user, whereby during intercourse, compression of said first chamber inflates said second chamber to apply stimulative force to the clitoral region of the user.

15. A sheet material comprising:
   a first generally planar layer of resilient material deformed in at least one portion thereof to form a first cavity of a first size, and deformed in at least a second portion thereof to form a second cavity of a second size substantially smaller than said first size, and deformed in a third portion thereof lying between said first and second portions to form a third cavity linking said first and second cavities, said first, second and third cavities all opening to one side of said first layer of material; and a second layer of material affixed to said one side of said first layer and forming closures for said first, second and third cavities such that said first cavity forms a first chamber of a first size, said second cavity forms a second chamber of a second size substantially smaller than the size of said first chamber, and said third cavity forms a channel linking said first and second chambers, said first and second chambers and said linking channel being filled with a fluid material whereby when a compressive force is applied to said first layer tending to compress said first chamber, the fluid contained therein is caused to pass through said linking channel into said second chamber causing the resilient material forming said second chamber to resiliently expand to substantially increase the size of said second chamber.

* * * * *